US010695285B2

United States Patent
Leclere

(10) Patent No.: US 10,695,285 B2
(45) Date of Patent: Jun. 30, 2020

(54) ANTI-POLLUTION COMPLEX COMPRISING CALENDULA EXTRACTS AND AN AQUEOUS EXTRACT OF LILUM CANDIDUM BULB AND USES THEREOF

(71) Applicant: MP2 COSMETIC SOLUTIONS SARL, Paris (FR)

(72) Inventor: Jacques Leclere, Saint-Gondon (FR)

(73) Assignee: MP2 COSMETIC SOLUTIONS SARL, Paris (FR)

( * ) Notice: Subject to any disclaimer, the term of this patent is extended or adjusted under 35 U.S.C. 154(b) by 0 days.

(21) Appl. No.: 15/777,805

(22) PCT Filed: Nov. 26, 2015

(86) PCT No.: PCT/IB2015/002367
§ 371 (c)(1),
(2) Date: May 21, 2018

(87) PCT Pub. No.: WO2017/089854
PCT Pub. Date: Jun. 1, 2017

(65) Prior Publication Data
US 2018/0344626 A1    Dec. 6, 2018

(51) Int. Cl.
| | | |
|---|---|---|
| *A61K 8/9794* | (2017.01) |
| *A61Q 19/08* | (2006.01) |
| *A61Q 17/00* | (2006.01) |
| *A61K 8/9789* | (2017.01) |
| *A61K 36/8967* | (2006.01) |
| *A61K 36/28* | (2006.01) |
| *A61K 8/81* | (2006.01) |

(52) U.S. Cl.
CPC .......... *A61K 8/9794* (2017.08); *A61K 8/8147* (2013.01); *A61K 8/9789* (2017.08); *A61K 36/28* (2013.01); *A61K 36/8967* (2013.01); *A61Q 17/00* (2013.01); *A61Q 19/08* (2013.01); *A61K 2800/48* (2013.01); *A61K 2800/522* (2013.01); *A61K 2800/5922* (2013.01)

(58) Field of Classification Search
CPC .. A61K 8/9794; A61K 8/8147; A61K 8/9789; A61K 36/8967; A61K 36/28; A61K 2800/48; A61K 2800/5922; A61K 2800/522; A61Q 17/00; A61Q 19/08
See application file for complete search history.

(56) References Cited

U.S. PATENT DOCUMENTS

| | | | |
|---|---|---|---|
| 6,221,372 B1 | 4/2001 | Golz Berner | |
| 2007/0140998 A1* | 6/2007 | Kato | A61K 8/345 424/62 |
| 2011/0256192 A1* | 10/2011 | Chevalier | A61K 8/732 424/401 |
| 2015/0104485 A1* | 4/2015 | Garcia Anton | C07K 5/1005 424/401 |

FOREIGN PATENT DOCUMENTS

| | | |
|---|---|---|
| FR | 1249468 | 12/1960 |
| GB | 2485483 | 5/2012 |
| WO | 99/16414 | 4/1999 |

OTHER PUBLICATIONS

K.C. Preethi et al: 11 Antioxidant Potential of an Extract of Calendula officinalis Flowers in Vitro and in Vivo Pharmaceutical Biology, vol. 44, No. 9, Jan. 1, 2006 (Jan. 1, 2006), pp. 691-697 abstract preparation of the extract; p. 692, left-hand column.
Zitterl-Eglseer K et al: 11 Anti-oedematous activities of the main triterpenediol esters of marigold (*Calendula officinalis* L.) Journal of Ethnopharmacology, Elsevier Ireland Ltd, IE, vol. 57, No. 2, Jan. 1, 1997 (Jan. 1, 1997), pp. 139-144.
Database GNPD [Online] MINTEL; Oct. 1, 2011 (Oct. 1, 2011), Maxima Inc.: 11 Fleur Vibrante Face Balm Concentre, XP002758047, Database accession No. 1664221 product description; manufacturer/ product website information; ingredients.
Database GNPD [Online] MINTEL; Aug. 1, 2007 (Aug. 1, 2007), Dr. Willer Pharma: "Marigold Ointment", XP002758048, Database accession No. 759205 product description; ingredients.
Database GNPD [Online] MINTEL; Dec. 1, 2009 (Dec. 1, 2009), Natura House: "Eye Contour Gel", XP002758049, Database accession No. 1222769 product description; ingredients.
Database GNPD [Online] MINTEL; Dec. 1, 2008 (Dec. 1, 2008), Laboratoire Alpaderm: "Nourishing Cream", XP002758050, Database accession No. 1024600 product description Calendula officinalis; Lilium Candidum; p. 5 ingredients.
Ageless Herbal Products: "Information on white lily—*Lilium candidum*", Internet Citation, Oct. 23, 2005 (Oct. 23, 2005), pp. 1-4, XP002738745, Retrieved from the Internet: URL:http://wayback. archive.org/web/20051023105011/http://www.ageless.co.za/herb-lily [retrieved on Apr. 21, 2015].
International Search Report dated May 26, 2016.

\* cited by examiner

*Primary Examiner* — Aradhana Sasan
*Assistant Examiner* — Quanglong N Truong
(74) *Attorney, Agent, or Firm* — IPSILON USA, LLP

(57) ABSTRACT

The invention relates to an anti-pollution complex comprising an aqueous extract of *Calendula*, an oily extract of *Calendula* and an aqueous extract of *Lilium candidum*, to a cosmetic topical composition comprising such an anti-pollution complex and to a cosmetic process to protect the skin from the harmful effects of pollution, in particular from the harmful effects of exhaust gases and heavy metals.

13 Claims, No Drawings

ANTI-POLLUTION COMPLEX COMPRISING CALENDULA EXTRACTS AND AN AQUEOUS EXTRACT OF LILUM CANDIDUM BULB AND USES THEREOF

RELATED APPLICATION

This application is a National Phase of PCT/IB2015/002367, filed on Nov. 26, 2015, the entirety of which is incorporated by reference.

BACKGROUND

Field of the Invention

The invention belongs to the technical fields of topical cosmetic products, in particular to cosmetic products for the skin.

In particular, the invention relates to an anti-pollution complex comprising an aqueous extract of *Calendula* (*Calendula officinalis* also known as pot marigold or *Calendula arvensis* also known as field marigold or wild marigold— these species of *Calendula* being generically denoted "*Calendula*" in the present application), an oily extract of *Calendula* and an aqueous extract of *Lilium candidum* (popularly known as the Madonna lily or white lily), to a cosmetic topical composition comprising such an anti-pollution complex and to a cosmetic process to protect the skin from the harmful effects of pollution, in particular from the harmful effects of exhaust gases and heavy metals.

Description of Related Art

Modern environmental conditions, such as heating and air conditioning, dryness, exposure to the sun, and atmospheric pollution, exert severe stress on the skin and accelerate the natural ageing process. Gas exhaust emissions appear amongst the most damaging pollutants.

The main air pollutants are classified into two distinct large families: primary pollutants and secondary pollutants.

Primary pollutants are directly emitted by the sources of pollution (traffic, industry, heating, agriculture . . . ). They consist of carbon oxides, sulphur oxides, nitrogen oxide, volatile organic compounds (VOCs), particulate matters (PM), in particular PM of diameter lower than 10 µm (PM10) and lower than 2.5 µm (PM 2.5), metals and in particular heavy metals (lead, mercury, cadmium . . . ).

Secondary pollutants are not directly emitted in the atmosphere but come from chemical reactions between gases such as ozone, nitrogen dioxide, sulphur dioxide, ammonia and with other secondary particles.

Some pollutants like the nitrogen dioxide or the particulate matters can be either primary or secondary pollutants.

All these pollutants are very harmful for the skin, which is the largest organ of the human body with a surface area of around 2 m². Oxidizing agents such as ozone or nitrogen oxides are irritants and generate free radicals. Particulates matters are often acidic and also irritant—they may lead to a reduction of the hydration of the skin and of oxygenation of the tissues. Carbon monoxide mainly coming from gas exhaust emissions produces tissue hypoxia. Sulphur dioxide causes alterations of the hydrolipidic film of the skin and irritations. Metals, and in particular heavy metals such as cadmium, mercury and lead, can interfere with cell metabolism, by altering enzymatically governed reactions. They reduce the activity of the cellular defense means against free radicals and contribute to oxidative damage with DNA and cellular lipid lesions. Thus the harmful effects of pollution on skin affect cell respiration and are reflected by accelerated ageing of the skin resulting in wrinkles, loss of firmness and elasticity, age spots, dryness, etc. . . .

Various cosmetic compositions have already been proposed to prevent the harmful effects due to pollutants (exhaust gases and/or heavy metals), in particular cosmetic compositions containing vegetable extracts.

As an example, U.S. patent application 2009/0035235 describes a cosmetic composition that is capable of combating and preventing the effects of atmospheric pollution on the skin containing two vegetable extracts: *Camellia sinensis* (white tea) and *Lapsana communis*. The composition containing these two extracts exhibits an antiradical activity, provides protection against lipoperoxidation caused by exhaust gases and stimulates the mitochondrial respiration.

However, with pollution on increase, there is still a need for other agents for effectively combating the harmful effects of pollutants on skin, in particular to prevent the degradation of cell respiration and accelerating ageing of the skin.

The aim of the invention is therefore to provide an anti-pollution cosmetic topical composition having at least these properties.

The studies performed by the inventors of the present invention have demonstrated that the combination of at least one aqueous extract of *Calendula*, of at least one oily extract of *Calendula* and of at least one aqueous extract of *Lilium Candidum* bulb has a synergistic activity on the prevention of the deleterious effects of pollution on the skin, in particular, such a combination has a synergistic activity on the stimulation of cell respiration and on the prevention of the decrease of the energetic level of the cell. In addition, such a combination has an efficient activity on the prevention of the oxidative stress. Such properties are particularly useful for combating the harmful effects of pollutants on skin, in particular the harmful effects of exhaust gases and heavy metals. Finally, at this combination has no cytotoxic effect at the tested amounts.

*Calendula* is a genus of about 15-20 species of annual and perennial herbaceous plants in the daisy family Asteraceae. They are native to southwestern Asia, western Europe, Macaronesia, and the Mediterranean and very resistant to negative temperatures (up to −20° C.). The most commonly cultivated and used member of the genus is the pot marigold (*Calendula officinalis*). Plant pharmacological studies have suggested that *Calendula* extracts have antiviral, antigenotoxic, and anti-inflammatory properties in vitro (Jimenez-Medina, E., et al., 2006, BMC Cancer. 6:6). In herbalism, *Calendula* in suspension or in tincture is used topically for treating acne, reducing inflammation, controlling bleeding, and soothing irritated tissue (Duran, V et al., Int J Tissue React., 2005, 27 (3), 101-106 and Pommier, P., et al., J. Clin. Oncol., 2004, 22(8) 1447-1453). Very recently, it has been reported that the flowers of *Calendula*, in the form of decoctions can be used topically for burns, bruises and other skin diseases since marigold extract exhibit antioxidants and anti-inflammatory activities due to the phenolic and flavonoid content of its ethanolic extracts (Kanlayavattanakul, Mayuree, and Nattaya Lourith, "*An update on cutaneous aging treatment using herbs*", Journal of Cosmetic and Laser Therapy, Accepted for publication: 1-31, May 2015).

*Lilium candidum* is a plant in the true lily family. It is native to Greece, the western Balkans and the Middle East, and naturalized in other parts of Europe (France, Italy, Ukraine, etc.) as well as in North Africa, the Canary Islands, Mexico, and other places. It forms bulbs at ground level, and unlike other lilies, has a basal rosette of leaves through the winter, which die back in summer A leafy flower stem, typically up to 1.2 meters high, emerges in late spring and bears sweetly and headily fragrant flowers in summer Flowers are white, flushed yellow at the base. The chemical composition of bulbs (saponins and polysaccharides) give the extract soothing, anti-inflammatory and protective properties. The extract also has hydrating and emollient properties (polysaccharides). Soluble polysaccharides have a filmogenic action on skin, which promotes ceramides production and skin hydration (see for example EP 0 993 822). They act by holding water, consequently maintaining the right moisture level in the horny layer, which in turn improves skin flexibility.

Objects and Summary

However, it was not known that the combination of at least one aqueous extract of *Calendula*, of at least one oily extract of *Calendula* and of at least one aqueous extract of *Lilium Candidum* bulb would have a synergistic activity on the prevention of the deleterious effects of pollution on the skin, in particular, that such a combination would have a synergistic activity on the stimulation of cell respiration and on the prevention of the decrease of the energetic level of the cell.

A first object of the present invention is thus an antipollution complex comprising:
  at least one aqueous extract of *Calendula* flowers,
  at least one oily extract of *Calendula* flowers, and
  at least one aqueous extract of *Lilium candidum* bulb.

A second object of the present invention is the use of the complex defined according to the first object of the present invention, as cosmetic anti-pollution ingredient useful to combat and substantially prevent the harmful effects of the pollution on the skin in a cosmetic topical composition.

A third object of the present invention is a topical cosmetic composition comprising an anti-pollution complex as defined in the first object of the invention.

A fourth object of the present invention, is a method of cosmetic care, for combating and substantially preventing the harmful effects of the pollution on the skin, in particular the harmful effects of exhaust gases and heavy metals, said method comprising at least one step of applying on the skin of a person in need thereof an affective amount of a topical cosmetic composition comprising an anti-pollution complex as defined as the first object of the invention.

Finally, a fifth object of the present invention is the non therapeutic use of a cosmetic topical composition comprising an anti-pollution complex as defined as the first object of the invention, for combating and substantially preventing the harmful effects of the pollution on the skin, in particular the harmful effects of exhaust gases and heavy metals.

The aqueous extract of *Calendula* flowers may be prepared by maceration of dried flowers of *Calendula officinalis* or *Calendula arvensis* in pure water during several hours at room temperature, typically from about 10 to 24 hours. After the maceration step, the aqueous macerate is cooled at a temperature ranging from about 2 to 8° C., typically at a temperature of about 4° C. and then filtered. The dry matter content of such an aqueous extract of *Calendula* flowers generally ranges from about 2.5 to about 2.7 weight % when 100 g of dried flowers are used for 1 L of pure water. The aqueous extract of *Calendula* flowers comprises, among other ingredients, oleanolic acid, vanillic acid and caprylic acid. It has the following characteristics:
  Dry matter content: 2.5 to 2.7 w. %
  pH: 4.0 to 6.0
  Refractive index: 1.330 to 1.380
  Density: 0.950 to 1.050
  Isorhamnetin-3-O-rutinoside: 0.1 to 0.26 g/l The oily extract of *Calendula* flowers may be prepared by maceration of dried flowers in alcohol, e.g. ethanol, during several hours at room temperature, typically during about 10 to 24 hours. After the maceration step, the alcoholic macerate is filtered. The dry matter content of such an alcoholic extract of *Calendula* flowers generally ranges from about 0.6 to about 0.8 weight % when 100 g of dried flowers are used for 1 L of alcohol. An oily phase is then added to the filtrate before total evaporation of the alcohol. As example of oily phase, one can mention mixtures of caprylic/capric triglycerides sold for example under the names Miglyol® or Mirytol®, and oleic sunflower oil (Aldivia). The oily extract of *Calendula* flowers comprises, among other ingredients, carotenoids, flavonoids and triterpendiols, in particular faradiol and faradiol esters.

The aqueous extract of white lily bulb may be prepared by maceration of frozen and then ground white lily bulb in pure water during several hours at room temperature, typically during about 10 to 24 hours. After the maceration step, the aqueous macerate is boiled during several hours, typically during about 10 to 12 hours and then hot filtered. The dry matter content of such an aqueous extract of white lily bulb generally ranges from about 1.0 to about 1.4 weight % when 100 g of frozen and ground white lily bulb are used for 1 L of pure water. This aqueous extract is then concentrated until the dry matter content reaches about 50% by weight. The aqueous extract of white lily bulb comprises, among other ingredients, 30 w. % of polysaccharides (on the basis of the total amount of dry matters).

According to a preferred embodiment of the invention, the anti-pollution complex comprises:
  from about 0.5 to 30 weight % (w. %), more preferably from about 15 to 25 w. %, of an aqueous extract of *Calendula* flowers,
  from about 0.5 to 30 w. %, more preferably from about 15 to 25 w. %, of an oily extract of *Calendula* flowers,
  from about 0.5 to 30 w. %, more preferably from about 15 to 25 w. %, of an aqueous extract of *Lilium candidum* bulb,
  from about 0.1 to 5 w. %, more preferably from about 2 to 5 w % of a thickening agent, and
  a sufficient amount of water to complete the total weight up to 100 w. %.

The thickening agent may be chosen among the components usually employed to increase the viscosity of cosmetic compositions and well known by those skilled in the art. Among such thickening agents, one can mention polymers such as polyacrylates (Carbomers), polyacrylamides, xanthan gum, carrageenan, cellulose derivatives such as hydroxyethylcellulose, etc . . . , and mineral thickeners such as silica. Among these thickening agent, polyacrylates are preferred.

According to a particulate and preferred embodiment of the present invention, the anti-pollution complex comprises:
  about 20 w. %, of an aqueous extract of *Calendula* flowers,
  about 20 w. %, of an oily extract of *Calendula* flowers,
  about 20 w. % of an aqueous extract of *Lilium candidum* bulb,
  from about 2 to 5 w. % of a polyacrylate, such as sodium polyacrylate,
  a sufficient amount of water to complete the total weight up to 100 w. %.

In addition to the above-mentioned ingredients, the anti-pollution complex according to the invention may also further comprise one or more additives, such as preservatives, colorants, perfumes, etc . . .

The anti-pollution complex according to the invention can be simply prepared by mixing each extract, optional ingredients and water, for example with a mechanical agitator.

At the end of its preparation, the anti-pollution complex according to the invention can be readily used as an anti-pollution agent useful to combat and substantially prevent the harmful effects of the pollution on the skin in a cosmetic topical composition or stored for an ulterior use.

According to a preferred embodiment of the invention, the amount of the anti-pollution complex in the topical cosmetic composition constituting the third object of the present invention ranges from about 0.5 to 5 w. %, more preferably from about 1.5 to 3 w.%. According to a particulate and even more preferred embodiment of the present invention, the amount of the anti-pollution complex in the topical cosmetic composition is equal to about 2 w. %.

In addition to the anti-pollution complex, the topical cosmetic composition according to the invention may further comprise one or more additional active ingredients capable of reinforcing and/or completing the advantageous properties of the anti-pollution complex. At the occasion, those skilled in the art will take care that this (these) additional active ingredient(s) does (do) not interfere or decrease advantageous properties of the anti-pollution complex.

The additional active ingredients may for example be chosen among vegetable extracts such as green tea and grape seed extracts, soy isoflavones extract, vitamins such as vitamin C (ascorbic acid), vitamin E (tocopheryl acetate) and vitamin B3 (niacinamide), hyaluronic acid, hexylresorcinol, retinol, alpha hydroxy acids, resveratrol, ceramides, fatty acids such as linoleic/linolenic acids and phospholipids, etc. . . .

The topical cosmetic composition according to the present invention is very well tolerated by the skin, they exhibit no photo toxicity and their application on the skin, even for extended periods of time, does not lead to any systemic effect.

The topical cosmetic composition may be presented into various galenic formulations adapted to a topical application, in particular in the form of gel, emulsion (e.g. cream or milk), oil-in-water or water-in-oil bi-phasic emulsions, mask, lotion, concentrated solution, serum, nanocapsules, liposomes, lipsticks, etc. . . . , such galenic formulations further comprising one or more classical excipients and carriers compatible with a topical cosmetic use. The topical cosmetic composition according to the invention is preferably in the form of a cream, a serum, a lotion or a gel.

In particular, the topical cosmetic composition according to the invention may further comprise one or more formulation agents or additives such as, as a non-limiting example, penetrating agents such as phytantriol and octyl dodécanol, thickening agents such as natural gums and synthetic polymers, surfactants, demulcents such as cetearyle octanoate, isopropyl myristate, cetearyle isononanoate, dimethicone, cyclomethicone, emulsifying agents such as polyglycerol derivatives, preservatives agents such as phenoxyethanol and dehydroacetic acid, oils, UV-A and UV-B filters, pigments such as titanium dioxide and zinc dioxide, dyes, film-forming agents, mineral charges, perfumes, etc. . . .

According to the method of cosmetic care according to the fifth object of present invention, the topical cosmetic composition can be applied once or twice a day on the skin of a person in need thereof, in particular on the face.

DETAILED DESCRIPTION

The following examples are provided by way of example and cannot be interpreted as limiting the scope of the present invention. They relate to the preparation of an anti-pollution complex, to the assessment of the synergistic anti-cytotoxicity properties of the anti-pollution complex according to the invention and its effects on energetic metabolism, to the assessment of the effect of the anti-pollution complex on ATP synthesis rate, to the assessment of the antiradical properties of the anti-pollution complex and to topical cosmetic compositions included in the present application.

EXAMPLES

Example 1: Preparation of an Anti-Pollution Complex According to the Present Invention 1. Preparation of an Aqueous Extract of *Calendula* Flowers 100 of dry flowers of *Calendula officinalis* have been macerated in 1 L of pure water during 12 hours at room temperature. The macerate has then been cooled until a temperature of 4° C. and then filtrated on a filter paper.

An aqueous extract of *Calendula* having the following characteristics has been obtained:

Dry matter content: 2.5 to 2.7 w. % pH: 5

Refractive index: 1.350

Density: 1.050

Isorhamnetin-3-O-rutinoside: 0.15 g/l

2. Preparation of an Oily Extract of *Calendula* Flowers 100 of dry flowers of *Calendula officinalis* have been macerated in 1 L of ethanol during 12 hours at room temperature and then filtered on a filter paper. The dry matter content of the filtrate was equal to 0.8 w. %. 500 mL of a mixture of caprylic/capric triglycerides sold under the tradename Mirytol® 318 by the firm BASF have then been added to the filtrate and ethanol evaporated from the mixture in a rotary vacuum evaporator at a temperature of about 60° C. The oily extract of *Calendula* flowers had the following characteristics:

Refractive index: 1.440 to 1.460

Peroxide index: <5.00

Acid index: <5.00

3. Preparation of an Aqueous Extract of *Lilium candidum* Bulb 100 g of fresh bulb of *Lilium candidum* were ground in a mortar and then macerated in 1 L of pure water for 12 hours at a temperature of 4° C. The mixture was then boiled during 12 hours and hot filtered on a paper filter. The dry matter content of the filtrate was 1.4 w. %. The resulting filtrate has thus been concentrated by evaporation until the dry matter content reached 50 w. %. The amount of polysaccharides in this concentrate was 30 w. % with regard to the total dry matter content.

4. Preparation of an Anti-Pollution Complex

An anti-pollution complex according to the first object of the present invention, having the following composition has then been prepared:

| | |
|---|---|
| aqueous extract of Calendula flowers prepared at step 1 | 20 w. % |
| oily extract of Calendula flowers prepared at step 2 | 20 w. % |
| aqueous extract of *Lilium candidum* bulb prepared at step 3 | 20 w. % |
| sodium polyacrylate | 2.8 w. % |
| pure water   qs | 100.0 w % |

The different ingredients have been mixed with a mechanical agitator.

Example 2: Assessment of the Synergistic Properties of the Anti-Pollution Complex According to the Invention Against the Harmful Effects of Exhaust Gases In this example, the anti-cytoxicity properties of the anti-pollution complex prepared in example 1 and its effects on the energetic metabolism after exposure of human keratinocytes in culture to exhaust gases have been tested.

2.1 Cytotoxicity Study

The aim this study was to demonstrate the reversibility of the cytotoxic effect of the exhaust gases after treatment with the anti-pollution complex according to the invention comprising the combination of the 3 extracts (aqueous extract of *Calendula* flowers, oily extract of *Calendula* flowers and aqueous extract of *Lilium candidum* bulb) compared to the effect of each of these extracts used individually.

This test was conducted using the Formazan blue assay (MTT). The keratinocyte cultures are obtained from human foreskin cells collected during circumcision and amplified in KGM2 medium (Clonetics) supplemented with insulin, EGF and pituitary extract.

After 24 hours of incubation in the presence or absence of the product being studied at different concentrations, the wells containing the cells were emptied by slowly turning them over and the cell layer was then rinsed with the culture medium. 200 μL of a diluted MTT solution were distributed in all the wells. The plates were then incubated at 37° C. for 2 to 4 hours. The formation of Formazan blue crystals could then be observed, in a quantity in inverse proportion to the succinate dehydrogenases obtained. The well were then emptied again by slowly turning them over. The cells were then lysed and the Formazan blue crystals dissolved, by adding 200 μL of dimethyl sulfoxide (DMSO). After homogenizing the color, by agitation, the plates were observed at 570 nm using a spectrophotometer.

The exhaust gases were produced by a motor. The gases were placed in contact with keratinocytes in culture for 2 hours the cells were then incubated with or without the product being studied for a further 22 hours.

The different product tested were as follows:

APC: Anti-pollution complex according to the present invention and as prepared in example 1, AECF: aqueous extract of *Calendula* flowers alone: this comparative composition (not forming part of the invention) was identical to the anti-pollution complex prepared in example 1 except that the combinations of the 3 extracts was replaced with 60 w. % of the aqueous extract of *Calendula* flowers prepared in step 1 of example 1, OECF: aqueous extract of *Calendula* flowers alone: this comparative composition (not forming part of the invention) was identical to the anti-pollution complex prepared in example 1 except that the combinations of the 3 extracts was replaced with 60 w. % of the oily extract of *Calendula* flowers prepared in step 2 of example 1, AELcB: aqueous extract of *Lilium candidum* bulb alone: this comparative composition (not forming part of the invention) was identical to the anti-pollution complex prepared in example 1 except that the combination of the 3 extracts was replaced with 60 w. % of the aqueous extract of *Lilium candidum* bulb prepared in step 3 of example 1.

Batch 1: Negative control not receiving any product,

Batch 2: Positive control: cells exposed to the exhaust gases, Batch 3: cells exposed to the exhaust gases and then treated with APC at 1.0% by weight, Batch 4: cells exposed to the exhaust gases and then treated with APC at 2.0% by weight, Batch 5: cells exposed to the exhaust gases and then treated with AECF at 1.0% by weight, Batch 6: cells exposed to the exhaust gases and then treated with AECF at 2.0% by weight, Batch 7: cells exposed to the exhaust gases and then treated with OECF at 1.0% by weight, Batch 8: cells exposed to the exhaust gases and then treated with OECF at 2.0% by weight, Batch 9: cells exposed to the exhaust gases and then treated with AELcB at 1.0% by weight, Batch 10: cells exposed to the exhaust gases and then treated with AELcB at 2.0% by weight.

For each batch, 6 measures have been made. The reversibility of effect of exhausts gases has been calculated by comparing the viability of the cells after exposure to exhausts gases but with no product (Positive control—Batch 2) to the viability of the cells after exposure to exhaust gases and treatment with each of the tested products.

2.2. Results of the Cytotoxicity Study

The results are reported in table 1 below:

TABLE 1

| Product | Optical density | Viability (%) |
|---|---|---|
| Batch 1: Negative control | 0.510 ± 0.012 | 100 |
| Batch 2: Positive control | 0.281 ± 0.019 | −45 * |
| Batch 3 Exhaust gases APC 1.0% | 0.324 ± 0.013 | +15 ** |
| Batch 4 Exhaust gases APC 2.0% | 0.360 ± 0.020 | +28 ** |
| Batch 5 Exhaust gases AECF 1.0% | 0.296 ± 0.013 | +5 (ns) |
| Batch 6 Exhaust gases AECF 2.0% | 0.312 ± 0.008 | +11 ** |
| Batch 7 Exhaust gases OECF 1.0% | 0.312 ± 0.010 | +17 ** |
| Batch 8 Exhaust gases OECF 2.0% | 0.328 ± 0.017 | +17 |
| Batch 9 Exhaust gases AELcB 1.0% | 0.306 ± 0.012 | +9 (ns) |
| Batch 10 Exhaust gases AELcB 2.0% | 0.319 ± 0.013 | +13 ** | ns: not significant
* significantly different compared to the negative control $p < 0.05$
** significantly different compared to positive control $p < 0.05$ These results show that the anti-pollution complex according to the invention, i.e. containing the combination of an aqueous extract of *Calendula* flowers, an oily extract of *Calendula* flowers and an aqueous extract of *Lilium candidum* bulb has a synergistic activity on the reversibility of the cytotoxicity induced by exhaust gas when cells are treated with 1 w. % of the complex (+15%) or with 2 w. % of the complex (+28%). This increase of the cell viability is higher than the cell viability obtained with the treatment of the cells with an equivalent amount of each extract individually demonstrating the synergistic effects of the combination of the 3 extracts. This synergistic effect is particularly noticeable when the anti-pollution complex is used at a concentration of 2 w. % (+28% versus +11%, +17% and +13% respectively for the extracts used individually at the same concentration.

2.3 Study of the Effect of the Anti-Pollution Complex on the Respiration Rate

The respiration rate is the consumption of oxygen in picoatoms per millions cells and per minute.

The keratinocyte cultures are obtained from human foreskin cells collected during circumcision and amplified in KGM2 medium (Clonetics) supplemented with insulin, EGF and pituitary extract.

The exhaust gases has been produced by a motor. The cells were placed in contact with the gases for 2 hours. They were then incubated with or without the product to be tested for a further 20 minutes. The study was conducted under 2 different conditions:

i) effect on the basal cellular respiration rate in non-permeabilised cells in the presence of glucose, ii) effect on the mitochondrial respiration rate of permeabilised cells in the presence of the pyruvate-malate substrate.

This study was conducted on keratinocytes in culture dissociated in trypsin. 5 to 10 million keratinocytes in culture were placed in suspension in 1 mL of Hanks-Hepes medium at a temperature of 30° C. containing 20 mM of glucose (basal respiration) or pyruvate (10 mM) and malate (10 mM) (mitochondrial respiration). Respiration was monitored in real time and given in picoatoms of oxygen consumed per minute and per $10^6$ cells. Adding different quantities of the product to the tank of an oxygraph shows possible stimulation or inhibition of respiration.

The amount of oxygen dissolved in the incubation medium was determined using a Clark electrode. The oxygen diffused through a Teflon® film is reduced at a polarized platinum cathode at −0.8 V. Under these conditions, the current passing between this cathode and a silver anode is proportional to the oxygen concentration in the solution. The ion bridge is provided by a semi-saturated solution of KCl. The measurements are taken and processed by a microcomputer (IBM-PC).

The same Batches 1 to 10 as in experiment 2.1 above have been also tested here. For each batch, 4 measures have been made.

2.4. Results of the Effect of the Anti-Pollution Complex on the Respiration Rate The results on basal respiration are reported in table 2 below:

TABLE 2

| Product | Basal respiration (picoatoms of $O_2$/min/$10^6$ cells) | Difference with the control (%) |
| --- | --- | --- |
| Batch 1: Negative control | 1424 ± 54 | — |
| Batch 2: Positive control | 816 ± 47.7 | −43 * |
| Batch 3: Exhaust gases APC 1.0% | 1038 ± 29.9 | +27 ** |
| Batch 4: Exhaust gases APC 2.0% | 1128 ± 80.1 | +38 ** |
| Batch 5: Exhaust gases AECF 1.0% | 879 ± 81.9 | +8 (ns) |
| Batch 6: Exhaust gases AECF 2.0% | 919 ± 35.1 | +13 ** |
| Batch 7: Exhaust gases OECF 1.0% | 941 ± 46.1 | +15 ** |
| Batch 8: Exhaust gases OECF 2.0% | 989 ± 47.2 | +21 ** |
| Batch 9: Exhaust gases AELcB 1.0% | 907 ± 29.4 | +11 ** |
| Batch 10: Exhaust gases AELcB 2.0% | 946 ± 41.0 | +16 ** | ns: not significant
* significantly different compared to the negative control p <0.05
** significantly different compared to positive control p <0.05

These results show that the anti-pollution complex according to the invention, i.e. containing the combination of an aqueous extract of *Calendula* flowers, an oily extract of *Calendula* flowers and an aqueous extract of *Lilium candidum* bulb has a synergistic activity on the effect of exhaust gases on the basal respiration when cells are treated with 1 w. % of the complex (+27%) or with 2 w. % of the complex (+38%). This effect is higher than the effect obtained with the treatment of the cells with an equivalent amount of each extract taken individually demonstrating the synergistic effects of the combination of the 3 extracts. This synergistic effect is particularly noticeable when the anti-pollution complex is used at a concentration of 2 w. % (+38% versus +13%, +21% and +16% respectively for the extracts used individually at the same concentration.

The results on mitochondrial respiration are reported in table 3 below:

TABLE 3

| Product | Mitochondrial respiration (picoatoms of $O_2$/min/$10^6$ cells) | Difference with the control (%) |
| --- | --- | --- |
| Batch 1: Negative control | 994 ± 37 | — |
| Batch 2: Positive control | 608 ± 44 | −39 * |
| Batch 3: Exhaust gases APC 1.0% | 739 ± 58 | +21 ** |
| Batch 4: Exhaust gases APC 2.0% | 760 ± 34 | +25 ** |
| Batch 5: Exhaust gases AECF 1.0% | 638 ± 50 | +5 (ns) |
| Batch 6: Exhaust gases AECF 2.0% | 689 ± 51 | +13 ** |
| Batch 7: Exhaust gases OECF 1.0% | 678 ± 18 | +11 ** |
| Batch 8: Exhaust gases OECF 2.0% | 706 ± 21 | +16 ** |
| Batch 9: Exhaust gases AELcB 1.0% | 679 ± 21 | +12 ** |
| Batch 10: Exhaust gases AELcB 2.0% | 720 ± 28 | +18 ** | ns: not significant
* significantly different compared to the negative control p <0.05
** significantly different compared to positive control p <0.05

These results show that the anti-pollution complex according to the invention, i.e. containing the combination of an aqueous extract of *Calendula* flowers, an oily extract of *Calendula* flowers and an aqueous extract of *Lilium candidum* bulb has a synergistic activity on the effect of exhaust gases on the mitochondrial respiration when cells are treated with 1 w. % of the complex (+21%) or with 2 w. % of the complex (+25%). This effect is higher than the effect obtained with the treatment of the cells with an equivalent amount of each extract taken individually demonstrating the synergistic effects of the combination of the 3 extracts. This synergistic effect is particularly noticeable when the anti-pollution complex is used at a concentration of 2 w. % (+25% versus +13%, +16% and +18% respectively for the extracts used individually at the same concentration.

Example 3: Assessment of the Effect of the Anti-Pollution Complex According to the Invention on the Basal and Mitochondrial ATP Synthesis The test has been performed on keratinocyte cultures obtained from human foreskin cells collected during circumcision and amplified in KGM2 medium (Clonetics) supplemented with insulin, EGF and pituitary extract.

The aim this study is to assess the effect of the anti-pollution complex according to the invention comprising the combination of the 3 extracts (aqueous extract of *Calendula* flowers, oily extract of *Calendula* flowers and aqueous extract of *Lilium candidum* bulb) on the basal and mitochondrial ATP synthesis rate of keratinocytes in culture. This is determined by means of bioluminescence using the luciferin/luciferinase kit. The amount of newly synthetized and basal ATP in the various aliquots is measured by the light emitted during the following ATP consumption reaction:

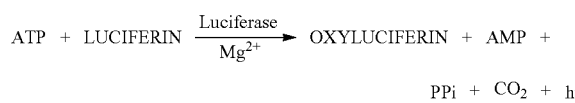

$$\text{ATP} + \text{LUCIFERIN} \xrightarrow[\text{Mg}^{2+}]{\text{Luciferase}} \text{OXYLUCIFERIN} + \text{AMP} + \text{PPi} + \text{CO}_2 + h\nu$$

The intensity of the light emitted during this reaction is measured using a luminometer (Luminoscan) with an ATP monitoring agent (ATP Bioluminescence Assay Kit HS II) from Boehringer Mannheim. This device transcribes the light emitted during the reaction into relative luminosity units (RLUs). The measured RLUs are converted into moles of ATP according to a standard ATP scale. The ATP synthesis rate is given in nmoles/min/$10^6$ cells. Keratinocytes in culture were cultivated in a $CO_2$ incubator at the rate of $10^6$ per run in an ADM culture medium (Clonetics).

The exhaust gases has been produced by a motor. The cells were placed in contact with the gases for 2 hours. They were then incubated with or without the product to be tested for a further 20 minutes under 2 conditions:

i) effect on the basal synthesis rate in non-permeabilised cells in the presence of glucose, ii) effect on the mitochondrial synthesis rate of permeabilised cells in the presence of the pyruvate-malate substrate.

The treatment consists in directly applying the anti-pollution complex as prepared in example 1 above at the desired concentration to the cells in suspension in the tank of an oxygraph. The cells at a concentration of $10^6$ cells/mL are placed in suspension in a "respiration buffer" (Hanks-Hepes glucose 20 mM), in the tank of the oxygraph with the thermostat set at 30° C. and agitated. For the determination of the mitochondrial synthesis rate the cells are permeabilised using digitonin. The addition of respiration substrate (glucose 20 mM for the basal synthesis rate/pyruvate 10 mM and malate 10 mM for the mitochondrial synthesis rate) allows the oxygen consumption rate to be observed (state 2 according to Chance). After adding different quantities of the anti-pollution complex (final concentrations 1 w. % and 2 w. %) to the tank of the oxygraph at regular intervals, one aliquot is taken from the tank of the oxygraph to titrate its ATP according to the method described above. The addition of different quantities of the anti-pollution complex according to the invention to the tank of the oxygraph therefore makes it possible to show the possible activation or inhibition of ATP synthesis For each tested concentration, 4 measures have been made.

The results are given in the following tables 4 and 5:

TABLE 4

| Product | ATP basal synthesis rate (nmol/min/$10^6$ cells) | Difference with the control (%) |
|---|---|---|
| Negative control | 6.53 ± 0.43 | — |
| Positive control | 4.93 ± 0.51 | −25 * |
| Anti-pollution complex at 1.0 w. % | 5.90 ± 0.14 | +20 ** |
| Anti-pollution complex at 2.0 w. % | 6.18 ± 0.21 | +25 ** |

TABLE 5

| Product | ATP mitochondrial synthesis rate (nmol/min/$10^6$ cells) | Difference with the control (%) |
|---|---|---|
| Negative control | 6.65 ± 0.30 | — |
| Positive control | 5.30 ± 0.48 | −20 * |
| Anti-pollution complex at 1.0 w. % | 6.30 ± 0.22 | +19 ** |
| Anti-pollution complex at 2.0 w. % | 6.68 ± 0.44 | +26 ** |

These results show that the anti-pollution complex according to the invention, i.e. containing the combination of an aqueous extract of *Calendula* flowers, an oily extract of *Calendula* flowers and an aqueous extract of *Lilium candidum* bulb stimulates the synthesis of ATP in keratinocytes after exposure to exhaust gases (+20% and +19% when cells are treated with 1 w. % of the complex and +25% and +26% with 2 w. % of the complex).

Example 4: Assessment of the Antiradical Properties of the Anti-Pollution Complex According to the Invention The aim of this study is to assess the antiradical properties of the anti-pollution complex according to the invention.

The test has been performed on keratinocyte cultures obtained from human foreskin cells collected during circumcision and amplified in KGM2 medium (Clonetics) supplemented with insulin, EGF and pituitary extract.

The exhaust gases has been produced by a motor. The cells were placed in contact with the gases for 2 hours. They were then incubated with or without the product to be tested for a further 24 hours.

The test has been conducted in triplicate after 24 hours of contact between the anti-pollution complex prepared as in example 1 and the cells at different concentrations (0.5 w. %, 1 w. % and 2 w. %).

The tests is based on the titration of malondialdehyde. Free radicals generate the lipid peroxidation process in an organism. Malondialdehyde (MDA) is one of the final products of polyunsaturated fatty acids peroxidation in the cells. An increase in free radicals causes overproduction of MDA.

Extraction of Malondialdehyde (MDA)

After 24 hours of contact between the complex and the cells, the latter were returned to suspension in a medium comprising the following ingredients:

250 µL of Tris buffer, 50 mM, pH 8 containing NaCl 0.1 M and EDTA 20 mM,

25 µL of sodium dodecylsulfate (SDS) at 7%

300 µL of HCl 0.1 N

38 µL of phosphotungstic acid at 1% in water,

300 µL of thiocarbituric acid (TBA) at 0.67% in water.

After 1 hour of incubation in the dark at 50° C. and cooling in ice-cold water, 300 mL of n-butanol was added to each tube. There were centrifuged at 10,000 g at 0° C. for 10 min. The top phase was recovered for titrating the MDA.

Titration of MDA

The MDA was titrated by measuring the fluorescence after separating the MDA-TBA complex by HPLC:

Bischoff Pump Model 2.200

Automatic Alcoot injector Model 788 autosampler

Ultrasep C18 column (30 cm×0.18 cm) 6 mm of porosity

Fluorescence detector, Jasco 821-F1.

The fluorescence detection was conducted with excitation at 515 nm and emission at 553 nm. The eluent used consisted of methanol:water, 40:60 (v/v) with pH adjusted to 6.3±0.5 using KOH 1 M. Quantification was performed using standards treated as the samples (0.125, 0.25, 0.5 and 1 mM) using an ICS software application (Pic 3) (Instrumentation, Consommable Service).

Protein Titration

The titration of the proteins has been carried out by the Bradford method using a spectrophotometer. The increase of absorbance at 595 nm is proportional to the concentration in proteins.

The results are given in the following table 6:

TABLE 6

| Product | MDA (μM/mg proteins) | Difference with the control (%) |
|---|---|---|
| Negative control | 666 ± 11 | — |
| Positive control | 927 ± 25 | +39 * |
| Anti-pollution complex at 0.5 w. % | 758 ± 52 | −18 ** |
| Anti-pollution complex at 1.0 w. % | 681 ± 52 | −27 ** |
| Anti-pollution complex at 2.0 w. % | 610 ± 50 | −34 ** |

\* significantly different compared to the negative control p <0.05
\*\* significantly different compared to positive control p <0.05

These results show that the anti-pollution complex according to the invention, i.e. containing the combination of an aqueous extract of *Calendula* flowers, an oily extract of *Calendula* flowers and an aqueous extract of *Lilium candidum* bulb has significant protective effect against free radicals, at the 3 tested concentrations.

Example 5: Moisturizing Milk

A moisturizing milk having the following composition has been prepared by conventional techniques well known from those of ordinary skilled in the art:

| | |
|---|---|
| Sodium phytate | 0.100 g |
| Glycerin | 5.000 g |
| Dehydroacetic acid | 0.150 g |
| Caprylic/capric triglycerids mixture sold under the name Mirytol ® 318 by BASF | 5.000 g |
| Glycerol monostearate | 0.500 g |
| Sunflower oil | 1.000 g |
| PEG 100 stearate | 3.000 g |
| Apricot kernel oil | 3.000 g |
| Dimethicone | 1.000 g |
| Tocopherol | 0.100 g |
| Caprylyl glycol | 0.500 g |
| Glyceryl caprylate | 0.500 g |
| Benzylic alcohol | 0.500 g |
| Carbomer sold under the name Carbopol ETD 2001 by Gattefossé | 0.100 g |
| Sodium hydroxide | 0.075 g |
| Perfume | 0.500 g |
| Anti-pollution complex prepared at example 1 | 0.500 g |
| Demineralized water qs | 100.000 g |

This milk has anti-pollution properties and can be applied once or twice a day on the skin.

Example 6: Anti-Pollution Facial Cream

A facial cream having the following composition has been prepared by conventional techniques well known from those of ordinary skilled in the art:

| | |
|---|---|
| Carbomer sold under the name Carbopol ETD 2001 by Gattefossé | 0.100 g |
| Tetrasodic EDTA | 0.100 g |
| Glycerin | 5.000 g |
| 1,2-hexanediol | 1.000 g |
| Caprylyl glycol | 0.500 g |
| Dehydroacetic acid | 0.150 g |
| Caprylic/capric triglycerids mixture sold under the name Mirytol ® 318 by BASF | 5.000 g |
| Shea butter | 2.500 g |
| Glycerol monostearate | 1.500 g |
| Cyclopentasiloxane | 1.000 g |
| Stearyl alcohol | 1.000 g |
| Sunflower oil | 1.000 g |
| Corn oil | 1.000 g |
| Apricot kernel oil | 1.000 g |
| Moringa oil | 1.000 g |
| Beeswax | 0.750 g |
| Ceteareth 33 | 0.750 g |
| Tocopherol | 0.100 g |
| Sodium hydroxide | 0.050 g |
| Perfume | 0.500 g |
| Anti-pollution complex prepared at example 1 | 2.000 g |
| Demineralized water qs | 100.000 g |

This facial cream has anti-pollution properties and can be applied once or twice a day on the skin.

The invention claimed is:

1. An anti-pollution complex comprising:
   from about 15 to 25 weight % (w. %) of at least one aqueous extract of *Calendula* flowers,
   from about 15 to 25 w. % of at least one oily extract of *Calendula* flowers, and
   from about 15 to 25 w. % of at least one aqueous extract of *Lilium candidum* bulb.

2. The anti-pollution complex according to claim 1, further comprising:
   from about 2 to 5 w. % of a thickening agent, and
   a sufficient amount of water to complete the total weight up to 100 w. %.

3. The anti-pollution complex according to claim 1, wherein it comprises:
   about 20 w. %, of an aqueous extract of Calendula flowers,
   about 20 w. %, of an oily extract of Calendula flowers,
   about 20 w. % of an aqueous extract of Lilium candidum bulb,
   from about 2 to 5 w. % of a polyacrylate,
   a sufficient amount of water to complete the total weight up to 100 w. %.

4. A method for combating and preventing the harmful effects of the pollution on the skin in a cosmetic topical composition, said method comprising applying a cosmetic anti-pollution complex according to claim 1.

5. A topical cosmetic composition comprising an anti-pollution complex as defined in claim 1.

6. The composition according to claim 5, wherein the amount of the anti-pollution complex ranges from about 0.5 to 5 w. %.

7. The composition according to claim 5, wherein the amount of the anti-pollution complex ranges from about 1.5 to 3 w. %.

8. The composition according to claim 5, wherein the amount of the anti-pollution complex is equal to about 2 w. %.

9. The composition according to claim 5, wherein it comprises one or more additional ingredients chosen among vegetable extracts, vitamins, hyaluronic acid, hexylresorcinol, retinol, alpha hydroxy acids, resveratrol, ceramides, fatty acids and phospholipids.

10. The composition according to claim 5, wherein it is the form of gel, emulsion, oil-in-water or water-in-oil biphasic emulsions, mask, lotion, concentrated solution, serum, nanocapsules, liposomes, lipsticks.

11. The composition according to claim 5, wherein it further comprises one or more formulation agents or additives.

12. The composition according to claim 11, wherein said agents or additives are chosen among penetrating agents, thickening agents, surfactants, demulcents, dimethicone, cyclomethicone, emulsifying agents, preservatives agents, oils, UV-A and UV-B filters, pigments, dyes, film-forming agents, charged minerals and perfumes.

13. A method of cosmetic care, for combating and preventing the harmful effects of the pollution on the skin, in particular the harmful effects of exhaust gases and heavy metals, said method comprising at least one step of applying on the skin of a person in need thereof an affective amount of a topical cosmetic composition as defined in claim 5.

\* \* \* \* \*